(12) United States Patent
Viray et al.

(10) Patent No.: US 8,550,086 B2
(45) Date of Patent: *Oct. 8, 2013

(54) RADIOPAQUE IMPLANT

(75) Inventors: Victor E. Viray, Sunnyvale, CA (US); Daniel Rogy, San Jose, CA (US); Doug C. Harrington, San Jose, CA (US); Jason John Umhoefer, Mountain View, CA (US); Matthew LaPlaca, Cumberland, RI (US); Jim Duronio, Westford, MA (US)

(73) Assignee: Hologic, Inc., Marlborough, MA (US)

( * ) Notice: Subject to any disclaimer, the term of this patent is extended or adjusted under 35 U.S.C. 154(b) by 438 days.

This patent is subject to a terminal disclaimer.

(21) Appl. No.: 12/773,332

(22) Filed: May 4, 2010

(65) Prior Publication Data

US 2011/0276070 A1 Nov. 10, 2011

(51) Int. Cl.
*A61F 6/06* (2006.01)
(52) U.S. Cl.
USPC .................. 128/831; 128/830; 606/213
(58) Field of Classification Search
USPC .............. 128/830–831; 606/191, 193, 197, 606/213; 604/515; 600/29, 32; 424/430; 623/1.1, 1.15
See application file for complete search history.

(56) References Cited

U.S. PATENT DOCUMENTS

| | | |
|---|---|---|
| 2,102,270 A | 12/1937 | Hyams |
| 3,680,542 A | 8/1972 | Cimber |
| 3,805,767 A | 4/1974 | Erb |
| 3,840,016 A | 10/1974 | Lindemann |
| 3,858,571 A | 1/1975 | Rudolph |
| 3,858,586 A | 1/1975 | Lessen |
| 3,918,431 A | 11/1975 | Sinnreich |
| 3,938,527 A | 2/1976 | Rioux et al. |
| 3,949,736 A | 4/1976 | Vrana et al. |
| 3,953,566 A | 4/1976 | Gore |
| RE29,345 E | 8/1977 | Erb |
| 4,052,754 A | 10/1977 | Homsy |
| 4,057,063 A | 11/1977 | Gieles et al. |
| 4,185,618 A | 1/1980 | Corey |
| 4,245,643 A | 1/1981 | Benzing, III et al. |
| 4,258,721 A | 3/1981 | Parent et al. |
| 4,311,145 A | 1/1982 | Esty et al. |

(Continued)

FOREIGN PATENT DOCUMENTS

| | | |
|---|---|---|
| AU | 59403 | 2/1997 |
| CA | 2182738 | 10/2000 |

(Continued)

OTHER PUBLICATIONS

International Search Report and Written Opinion mailed Apr. 8, 2008 for International Application No. PCT/US2007/085328 (7 pages).

(Continued)

*Primary Examiner* — Patricia Bianco
*Assistant Examiner* — Camtu Nguyen
(74) *Attorney, Agent, or Firm* — Vista IP Law Group LLP

(57) ABSTRACT

Implants for placement in the fallopian tube are provided that comprise radiopaque material. Implants include an inner core of silicone, a radiopaque material, an outer porous portion surrounding the inner core, and, optionally, a sound-reflecting air pocket. The implant may be detected in a fluoroscopic image and/or via ultrasound after placement of the implant in the fallopian tube.

6 Claims, 7 Drawing Sheets

(56) References Cited

U.S. PATENT DOCUMENTS

| | | | |
|---|---|---|---|
| 4,345,602 A | 8/1982 | Yoshimura et al. |
| 4,416,660 A | 11/1983 | Dafoe |
| 4,474,179 A | 10/1984 | Koch |
| 4,509,504 A | 4/1985 | Brundin |
| 4,512,342 A | 4/1985 | Zaneveld |
| 4,523,590 A | 6/1985 | Roth et al. |
| 4,537,186 A | 8/1985 | Verschoff et al. |
| 4,606,336 A | 8/1986 | Zeluff |
| 4,641,634 A | 2/1987 | Storz |
| 4,700,701 A | 10/1987 | Montaldi |
| 4,779,611 A | 10/1988 | Grooters et al. |
| 4,788,966 A | 12/1988 | Yoon |
| 4,793,326 A | 12/1988 | Shishido |
| 4,834,091 A | 5/1989 | Ott |
| 4,907,158 A | 3/1990 | Kettier et al. |
| 4,966,597 A | 10/1990 | Cosman |
| 4,994,069 A | 2/1991 | Ritchart et al. |
| 5,009,655 A | 4/1991 | Daignault, Jr. et al. |
| 5,026,342 A * | 6/1991 | Hammerstedt et al. ......... 600/35 |
| 5,095,917 A | 3/1992 | Vancaillie |
| 5,122,137 A | 6/1992 | Lennox |
| 5,147,353 A | 9/1992 | Everett |
| 5,152,784 A | 10/1992 | Tsilibary |
| 5,167,658 A | 12/1992 | Ensslin |
| 5,203,344 A | 4/1993 | Scheltinga et al. |
| 5,303,719 A | 4/1994 | Wilk et al. |
| 5,304,194 A | 4/1994 | Chee et al. |
| 5,320,091 A | 6/1994 | Grossi et al. |
| 5,341,807 A | 8/1994 | Nardella |
| 5,366,476 A | 11/1994 | Noda |
| 5,383,922 A | 1/1995 | Zipes et al. |
| 5,391,146 A | 2/1995 | That et al. |
| 5,395,342 A | 3/1995 | Yoon |
| 5,458,585 A | 10/1995 | Salmon et al. |
| 5,458,640 A | 10/1995 | Gerrone |
| 5,460,628 A | 10/1995 | Neuwirth et al. |
| 5,469,857 A | 11/1995 | Laurent et al. |
| 5,490,845 A | 2/1996 | Racz |
| 5,505,686 A | 4/1996 | Willis et al. |
| 5,531,741 A | 7/1996 | Barbacci |
| 5,536,267 A | 7/1996 | Edwards et al. |
| RE35,330 E | 9/1996 | Malone et al. |
| 5,556,396 A | 9/1996 | Cohen et al. |
| 5,569,242 A | 10/1996 | Lax et al. |
| 5,569,245 A | 10/1996 | Guglielmi et al. |
| 5,569,462 A | 10/1996 | Martinson et al. |
| 5,581,487 A | 12/1996 | Kelly et al. |
| 5,589,176 A | 12/1996 | Seare, Jr. |
| 5,601,600 A | 2/1997 | Ton |
| 5,605,693 A | 2/1997 | Seare, Jr. |
| 5,617,319 A | 4/1997 | Arakawa et al. |
| 5,632,767 A | 5/1997 | Sinofsky |
| 5,635,482 A | 6/1997 | Bhatnagar |
| 5,643,253 A | 7/1997 | Baxter et al. |
| 5,643,257 A | 7/1997 | Cohen et al. |
| 5,649,924 A | 7/1997 | Everett et al. |
| 5,658,282 A | 8/1997 | Daw et al. |
| 5,673,704 A | 10/1997 | Marchlinski et al. |
| 5,743,905 A | 4/1998 | Eder et al. |
| 5,746,769 A | 5/1998 | Ton et al. |
| 5,785,705 A | 7/1998 | Baker |
| 5,785,706 A | 7/1998 | Bednarek |
| 5,800,529 A | 9/1998 | Brauker et al. |
| 5,810,810 A | 9/1998 | Tay et al. |
| 5,827,269 A | 10/1998 | Saadat |
| 5,830,222 A | 11/1998 | Makower |
| 5,836,875 A | 11/1998 | Webster, Jr. |
| 5,836,990 A | 11/1998 | Li |
| 5,891,457 A | 4/1999 | Neuwirth et al. |
| 5,935,137 A | 8/1999 | Saadat et al. |
| 5,954,715 A | 9/1999 | Harrington et al. |
| 5,979,446 A | 11/1999 | Loy |
| 6,042,590 A | 3/2000 | Sporri et al. |
| 6,059,779 A | 5/2000 | Mills |
| 6,066,139 A | 5/2000 | Ryan et al. |
| 6,068,626 A | 5/2000 | Harrington et al. |
| 6,071,283 A | 6/2000 | Nardella |
| 6,080,152 A | 6/2000 | Nardella |
| 6,091,995 A | 7/2000 | Ingle et al. |
| 6,096,052 A | 8/2000 | Callister et al. |
| 6,145,505 A | 11/2000 | Nikolchev et al. |
| 6,176,240 B1 | 1/2001 | Nikolchev et al. |
| 6,203,568 B1 * | 3/2001 | Lombardi et al. ........... 623/1.13 |
| 6,264,653 B1 | 7/2001 | Falwell |
| 6,309,384 B1 | 10/2001 | Harrington et al. |
| 6,346,102 B1 | 2/2002 | Harrington et al. |
| 6,391,024 B1 | 5/2002 | Sun et al. |
| 6,401,719 B1 | 6/2002 | Farley et al. |
| 6,432,116 B1 | 8/2002 | Callister et al. |
| 6,526,979 B1 | 3/2003 | Nikolchev et al. |
| 6,565,557 B1 | 5/2003 | Sporri et al. |
| 6,569,160 B1 | 5/2003 | Goldin et al. |
| 6,595,989 B1 | 7/2003 | Schaer |
| 6,634,361 B1 | 10/2003 | Nikolchev et al. |
| 6,637,962 B1 | 10/2003 | Roche et al. |
| 6,656,200 B2 * | 12/2003 | Li et al. .......... 606/191 |
| 6,679,266 B2 | 1/2004 | Nikolchev et al. |
| 6,682,477 B2 | 1/2004 | Boebel et al. |
| 6,684,884 B2 | 2/2004 | Nikolchev et al. |
| 6,705,323 B1 | 3/2004 | Nikolchev et al. |
| 6,709,667 B1 | 3/2004 | Lowe et al. |
| 6,712,810 B2 | 3/2004 | Harrington et al. |
| 6,726,883 B2 | 4/2004 | Ito et al. |
| 6,763,833 B1 | 7/2004 | Khera et al. |
| 6,780,182 B2 | 8/2004 | Bowman et al. |
| 6,871,085 B2 | 3/2005 | Sommer |
| 6,871,650 B1 | 3/2005 | Nikolchev et al. |
| 6,964,274 B1 | 11/2005 | Ryan et al. |
| 6,972,018 B2 | 12/2005 | Ryan et al. |
| 7,014,645 B2 * | 3/2006 | Greene et al. ............... 606/158 |
| 7,073,504 B2 | 7/2006 | Callister et al. |
| 7,195,630 B2 | 3/2007 | Ciarrocca |
| 7,220,259 B2 | 5/2007 | Harrington et al. |
| 7,237,552 B2 | 7/2007 | Khera et al. |
| 7,398,780 B2 | 7/2008 | Callister et al. |
| 7,428,904 B2 | 9/2008 | Nikolchev et al. |
| 7,506,650 B2 | 3/2009 | Lowe et al. |
| 7,582,085 B2 | 9/2009 | Bowman et al. |
| 7,635,382 B2 | 12/2009 | Pryor |
| 8,231,619 B2 * | 7/2012 | Callaghan et al. ............. 606/41 |
| 2002/0177855 A1 | 11/2002 | Greene, Jr. et al. |
| 2002/0188195 A1 | 12/2002 | Mills |
| 2003/0032936 A1 | 2/2003 | Lederman |
| 2004/0186423 A1 | 9/2004 | Cafferata |
| 2004/0255958 A1 | 12/2004 | Harrington et al. |
| 2004/0267308 A1 | 12/2004 | Bagaosian et al. |
| 2005/0045184 A1 | 3/2005 | Khera et al. |
| 2005/0143817 A1 | 6/2005 | Hunter et al. |
| 2006/0116635 A1 | 6/2006 | Van Heugten et al. |
| 2007/0135830 A1 | 6/2007 | Schaeffer |
| 2007/0173883 A1 | 7/2007 | Keegan et al. |
| 2007/0196158 A1 | 8/2007 | Roche et al. |
| 2008/0135053 A1 | 6/2008 | Gruber et al. |
| 2009/0056722 A1 | 3/2009 | Swann |
| 2009/0281558 A1 | 11/2009 | Li |
| 2011/0180073 A1 | 7/2011 | Callaghan et al. |
| 2011/0202077 A1 | 8/2011 | Chin et al. |

FOREIGN PATENT DOCUMENTS

| | | |
|---|---|---|
| DE | 3917179 | 12/1989 |
| EP | 0105669 B1 | 4/1984 |
| EP | 0153190 A1 | 8/1985 |
| EP | 0541258 B1 | 4/1993 |
| EP | 0752236 B1 | 1/1997 |
| EP | 1554999 A1 | 7/2005 |
| GB | 2359492 | 8/2001 |
| WO | 9640023 | 12/1996 |
| WO | 9640024 | 12/1996 |
| WO | 9717030 | 5/1997 |
| WO | 9749345 | 12/1997 |
| WO | 9855046 | 12/1998 |
| WO | 0191834 | 12/2001 |
| WO | 0228311 | 4/2002 |

OTHER PUBLICATIONS

International Search Report and Written Opinion mailed Nov. 16, 2009 for International Application No. PCT/US2009/057998 (5 pages).

International Search Report and Written Opinion mailed May 4, 2011 for International Application No. PCT/US2011/035189 (6 pages).

Dictionary.com; definition of coupled; retrieved Sep. 30, 2011 from http://dictionary.com/browse/coupled.

Brumsted, Attempted Transcervial Occlusion of the Fallopian Tube with teh ND:Yag Laser, 77 Obstetrics and Gynecology 327-328 (Feb. 1991).

Coleman, The Foreign Body Reaction: A Chronic Inflammatory Response, 8 J. Biomed. Mater. Res. 199-211 (1974).

Conceptus Incorporated Summary of Safety and Effectiveness Data, P020014, Nov. 4, 2002.

Kearney, Patent Cooperation Treaty Written Opinion, International Application No. PCT/US98/08111, Date of Mailing Feb. 22, 1999.

Neuwirth, Update on Transcervical Sterilization, 51 International Journal of Gynecology & Obstetrics, Suppl. 1, S23-28 (1995).

Phillips, Experimental Closure of Arteriovenous Fistula by Transcatheter Electrocoagulation, 115 Radiology 319-321 (May 1975).

Pollack, Wound Healing: A Review, 5:5 J. Dermatol. Surg. Oncol. 389 (May 1979).

Quinones Guerror, Tubal Electrocauterization Under Hysteroscopic Control, 7 Contraception 195-201 (Mar. 1973).

Quinones, Hysteroscopic Sterilization, 14 International Journal of Gynecology & Obstetrics 27-34 (1976).

Sahwl, The Leukocytic Response to an Intrauterine Foreign Body in the Rabbit, 22 Fertility and Sterility 398 (Jun. 1971).

Thompson, Vessel Occlusion with Transcatheter Electrocoagulation: Initial Clinical Experience, 133 Radiology 335-340 (Nov. 1979).

Tibbs, Wound Healing Following Radiation Therapy: A Review, 42 Radiology and Oncology 99-106 (1977).

* cited by examiner

RADIOPAQUE IMPLANT

FIELD OF THE INVENTION

The present invention relates to a radiopaque implant for placement in the fallopian tubes of a female patient and methods for using the radiopaque implant for sterilization. In particular, this invention is directed to a radiopaque implant that may be easily detected in a fluoroscopic image and/or via ultrasound after its placement in the fallopian tubes such that the location of the implant in the fallopian tubes may be detected and sterilization of the patient may be confirmed.

BACKGROUND

It is often desired or necessary for medical reasons to close the fallopian tubes of a female for sterilization purposes. One method for sterilization of females is the placement of an implant or device within the fallopian tubes to occlude them. Total occlusion of the fallopian tubes prevents male sperm from fertilizing female eggs, thus preventing conception. Such implants are usually placed in the uterotubal junction, the narrowest part of the fallopian tubes.

The proper placement of implants in the fallopian tubes, however, has often proven to be difficult. If the implant is placed in the wrong location, it may cause serious medical problems for the patient or it may result in the fallopian tubes not being completely occluded and the patient not being sterilized.

A physician will usually perform a hysterosalpingogram (HSG) at about six to twelve weeks after the initial implant of the device to confirm the proper placement of the implant. An HSG involves pressurizing the uterus with radiopaque fluid while taking a real-time fluoroscopic image. The HSG test is a radiology procedure usually done in the radiology department of a hospital in which radiopaque fluid (dye) is injected into the uterine cavity through the vagina and cervix. The uterine cavity fills with dye and if the fallopian tubes are open, the dye will then fill the tubes and spill out into the abdominal cavity. In this way, it may be determined whether or not the fallopian tubes are open or occluded and where the occlusion is located.

One possible disadvantage of the HSG procedure is that the prior art implants are not seen in a fluoroscopic image because they are not radiopaque. In other words, the presence of the implant in the fallopian tubes is confirmed by the contrast of the radiopaque fluid and not actually by the implant itself. As a result, confirmation of the implant in the fallopian tubes and the associated occlusion of the fallopian tubes is at least in part a function of how well the test is performed. That is, the person performing the test must understand not only proper HSG technique, but also the general intended placement of the implant to ensure that the radiopaque fluid (dye) is indeed reaching the area of the implant.

Another possible disadvantage is that radiologists, not gynecologists, often perform the HSG. Although radiologists understand the HSG procedure, gynecologists may have a better understanding of the general intended placement of the implant in the fallopian tubes.

Therefore, there is a need for implants that are radiopaque and able to be easily detected in the fluoroscopic image during an HSG. This would make the detection of the implant easier for a radiologist or any physician performing the HSG after the implant has been placed in the fallopian tubes.

It is an object of the present invention to produce a radiopaque implant to be placed in the fallopian tubes. More specifically, it is another object of this invention to produce an implant that may be detected by a fluoroscopic image, e.g., during an HSG.

Another procedure for verifying proper placement of the implant is using ultrasound either transvaginally (TVUS) or transabdominally (TAUS). In either case, the ultrasound is operated using the Doppler mode to detect fluid velocity in the fallopian tubes, indicating a patent tube. In other modes, an ultrasound contrast agent is employed to image the presence of the distension media and contrast agent in the fallopian tube, which would indicate a patent tube. Typically, the ultrasound contrast media used in verifying the proper placement of the implant contains a suspension of gas bubbles of various sizes. One such ultrasound contrast method that makes use of these bubbles is called hysterosalpingo-contrast-sonography (HyCoSy). HyCoSy uses microbubbles in liquid to evaluate fallopian tube patency with ultrasound. An advantage of HyCoSy over HSG is that many gynecologists possess ultrasound equipment in their offices.

Therefore, it is an object of the present invention to produce an implant to be placed in the fallopian tubes that is both radiopaque and detectable using ultrasound. More specifically, it is another object of this invention to produce an implant that may be detected by a fluoroscopic image, e.g., during an HSG, and/or by ultrasound, e.g., using HyCoSy.

SUMMARY OF THE INVENTION

In one aspect, the present invention is an implant for placement within a fallopian tube of a patient. The implant comprises silicone and radiopaque material that allows the implant to be detected and identified in a fluoroscopic image after implantation.

In another aspect, the present invention is an implant for placement within a fallopian tube of a patient comprising silicone, a radiopaque material, and sound-reflecting gas pockets. The radiopaque material allows the implant to be detected and identified in a fluoroscopic image after implantation. The sound-reflecting gas pockets allow the implant to be detected and identified using ultrasound after implantation.

In one aspect of the invention, the radiopaque implant may be used in a method to sterilize a female patient by ablating tissue within a fallopian tube of the patient, placing the radiopaque implant adjacent to the ablated tissue, and visualizing the radiopaque implant to confirm proper placement thereof within the fallopian tube. Tissue growth may occur around the implant within the fallopian tube to further occlude the fallopian tube. The implant is capable of being detected in a fluoroscopic image after placing the radiopaque implant in the fallopian tube.

In another aspect of the invention, the radiopaque and ultrasound-detectable implant may be used in a method to sterilize a female patient by ablating tissue within a fallopian tube of the patient, placing the radiopaque and ultrasound-detectable implant adjacent to the ablated tissue, and visualizing the radiopaque implant to confirm proper placement thereof within the fallopian tube. Tissue growth may occur around the implant within the fallopian tube to further occlude the fallopian tube. The implant is capable of being detected in a fluoroscopic image and/or via ultrasound after placing the implant in the fallopian tube.

In one embodiment of the invention, the radiopaque material employed may be a metal powder or a metal filament that is combined with a material such as silicone to make the implant. In this embodiment, the radiopaque implant comprises an inner core comprising silicone and a radiopaque material, and an outer porous portion surrounding the inner core.

In another embodiment of the invention, the radiopaque material employed may be a metal powder or a metal filament which is combined with a material such as with silicone to make the implant. In this embodiment, the radiopaque implant comprises an inner core comprising silicone and a radiopaque material, an outer porous portion surrounding said inner core, and sound-reflecting gas pockets.

These and other features, aspects, and advantages of the present invention will become better understood with regard to the following description, appended claims, and accompanying drawings.

DETAILED DESCRIPTION OF THE INVENTION

The present invention is directed to a radiopaque implant for placement within a fallopian tube of a patient. The term "radiopaque" refers to the relative inability of electromagnetism, particularly X-rays, to readily pass through a particular material. The term "radiopaque material" refers to a material that does not readily allow X-rays or similar radiation to pass such that the material may be seen on an x-ray image or a fluoroscopic image. The term "radiopaque implant" as it is used herein refers to the implant of the present invention comprising radiopaque material.

Radiopacity is a key consideration in the design of the implant because it allows the implant to be detected in a fluoroscopic image during an HSG after the implant is placed in the fallopian tubes. This is an important feature of the invention because it may confirm the placement of the implant in the fallopian tubes and also aid in determining whether or not the fallopian tubes are occluded and the patient is sterile.

Figure 1:
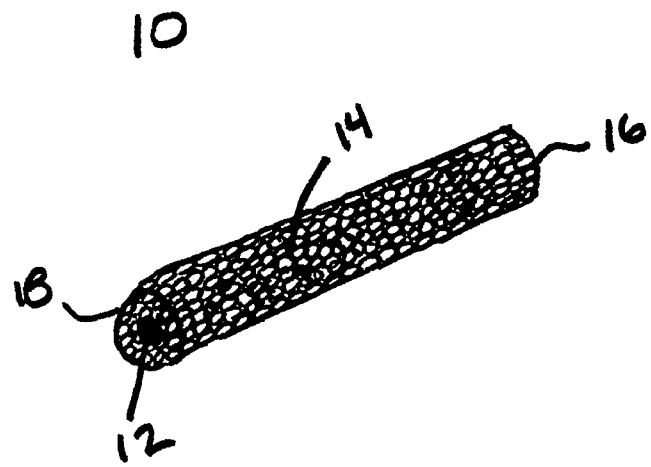
FIG. 1 is a highly-enlarged schematic perspective view of an implant according to one embodiment of the invention.

Referring to FIG. 1, an implant 10 of an embodiment of the present invention has an inner core 12 and an outer porous portion 14. The inner core 12 comprises any suitable matrix material and a radiopaque material. The matrix material may be, for example, silicone. The outer porous portion 14 may also be, for example, silicone. The inner core 12 has a distal end 16 and a proximal end 18. The outer porous portion 14 surrounds the inner core 12. In one aspect of the invention, the outer porous portion 14 is continuous along the length of the implant 10.

The overall cross-sectional shape of the radiopaque implant 10 may be round, oval, or any other suitable shape. An implant 10 may have, for example, a diameter of between about 1.0 mm and 2.0 mm, and preferably may have a diameter of about 1.6 mm. The diameter of the inner core 12 of the implant 10 may be, for example, between about 0.25 mm and 0.5 mm, and preferably may have a diameter of about 0.34 mm. Additionally, the overall length of the implants may be, for example, between about 2 mm and about 10 mm, and more preferably, between about 3 mm and about 6 mm.

The outer porous portion of the implant is preferably formed as a reticulated foam, meaning that the pores communicate with other pores, rather than exist as discrete and isolated voids within the material. Silicone foam is acceptable. Silicone foam is readily formed into the outer porous portion of the implant by employing the procedure set forth in U.S. Pat. No. 5,605,693 to Seare, "Method of Making A Porous Device," incorporated herein by reference in its entirety for all purposes. For example, uncured silicone, such as MED 4860 grade supplied by Nusil Technology Corporation, may be injected into a form packed with granules that slowly fills the voids between all the granules. The silicone may be cured and the particles dissolved in a suitable solvent. Silicone foam with a small pore size, such as 1-400 microns (preferably 40-400 microns) may be beneficial to enhance tissue growth in the pores of the foam in the fallopian tube. This will further occlude the fallopian tube for purposes of sterilization. In addition to silicone, other materials may be used to make the outer porous portion, such as ePTFE (also referred to as expanded Teflon or expanded polytetraflouroethylene), acrylic copolymer, cellulose acetate, polyethylene, high density polyethylene, and polyester.

In general, radiopaque materials suitable for use in this invention are materials that are biocompatible and that may be used to form an implant to be placed in the fallopian tubes. The radiopaque materials employed to produce the implant should not negatively affect any of the desired physical characteristics of the implant and should also be able to be processed with the other materials selected to be used to make the implant.

Radiopaque materials suitable for use in the present invention include metal particulates that are radiopaque and may be easily combined with materials such as silicone during processing of the implant. Examples of these radiopaque materials include the following: platinum, iridium, tungsten, tantalum, titanium, stainless steel, rhenium, barium, gold, and silver or the like and other metals that are well-known to those skilled in the art to be radiopaque. Alloys of any of the above-mentioned metals, such as platinum-iridium alloy, may also be suitable for use in this invention. The preferred materials useful in the present invention are tantalum and platinum.

Non-metal and other radiopaque materials, such as barium sulfate, may also be used in the present invention. Pure metal components, however, are preferred because they are much more dense than other radiopaque materials, such as barium sulfate. Any of the radiopaque materials may be added to the outer porous portion 14 in addition to the inner core 12 of the implant 10.

Figure 2:
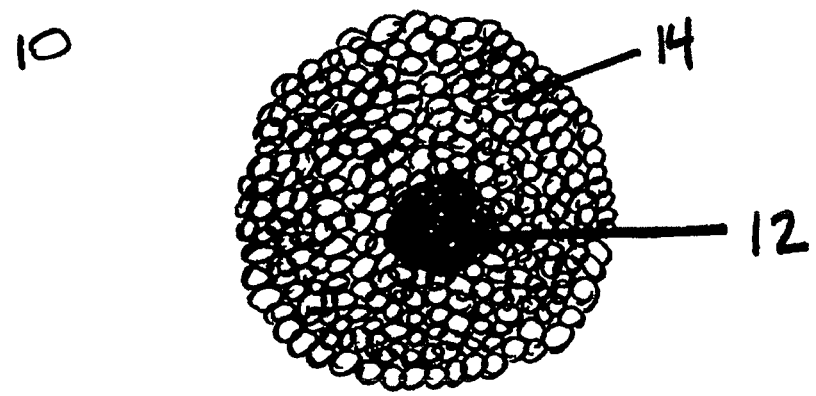
FIG. 2 is a schematic cross-sectional view taken radially of a radiopaque implant having an inner core and an outer porous portion surrounding the inner core.
Figure 3:
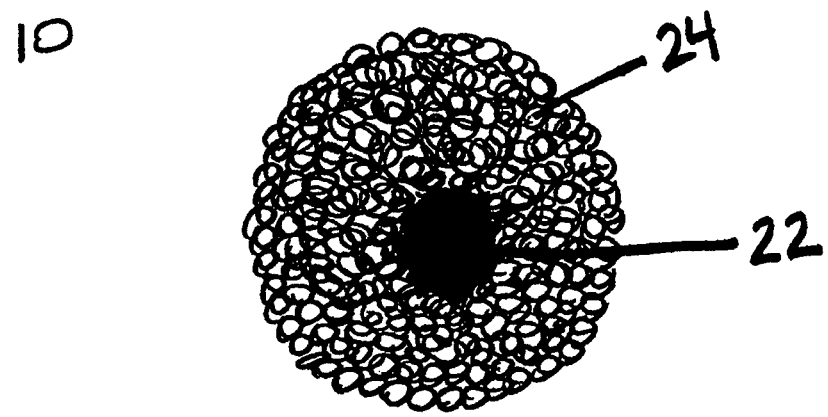
FIG. 3 is a schematic cross-sectional view taken radially of a radiopaque implant having a inner core comprising metallic powder.

A cross-sectional view of an implant 10 according to an embodiment of the present invention is shown in FIG. 2, where: the inner core 12 is solid and comprises silicone and radiopaque material, and the outer porous portion 14 is silicone foam. Other materials, however, in addition to silicone and the radiopaque material, may be used to form the implant. FIG. 3 depicts a schematic cross-sectional view taken radially of a radiopaque implant having an inner core comprising metallic powder (22).

Figure 5:
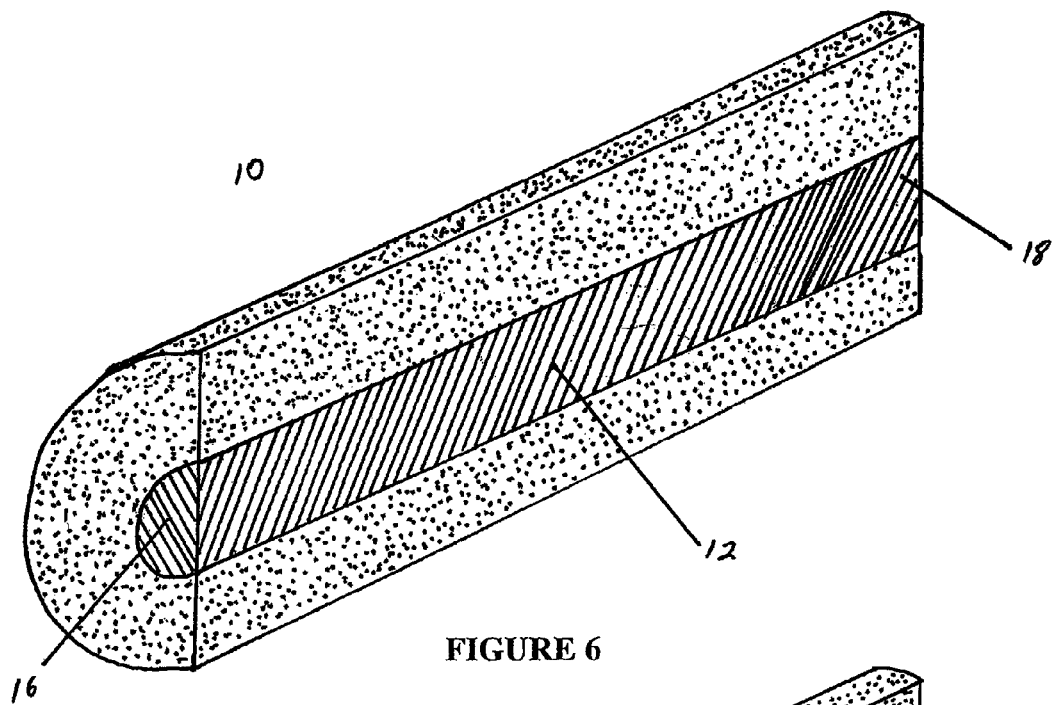
FIG. 5 is a schematic cross-sectional view taken longitudinally of a radiopaque implant having an inner core whose ends are uncapped.

Radiopaque material may be present in both the inner core 12 of the implant 10 and the outer porous portion 14. Whatever radiopaque material is selected, it may be blended with silicone and the resulting mixture may be used to make the inner core 12 of the implant. In one embodiment, depicted in FIG. 5, the ends 16 and 18 of the inner core 12 are uncapped and comprise radiopaque material and silicone. This occurs because the radiopaque material is added to the silicone continuously such that the radiopaque material is dispersed throughout the silicone. The radiopaque material is dispersed uniformly or non-uniformly throughout the silicone depending on the blending technique employed during the implant manufacture. In either instance, both the distal and proximal ends 16 and 18 of the inner core 12 are uncapped and comprise radiopaque material and silicone such that the radiopaque material is in contact with the fallopian tube.

Figure 6:
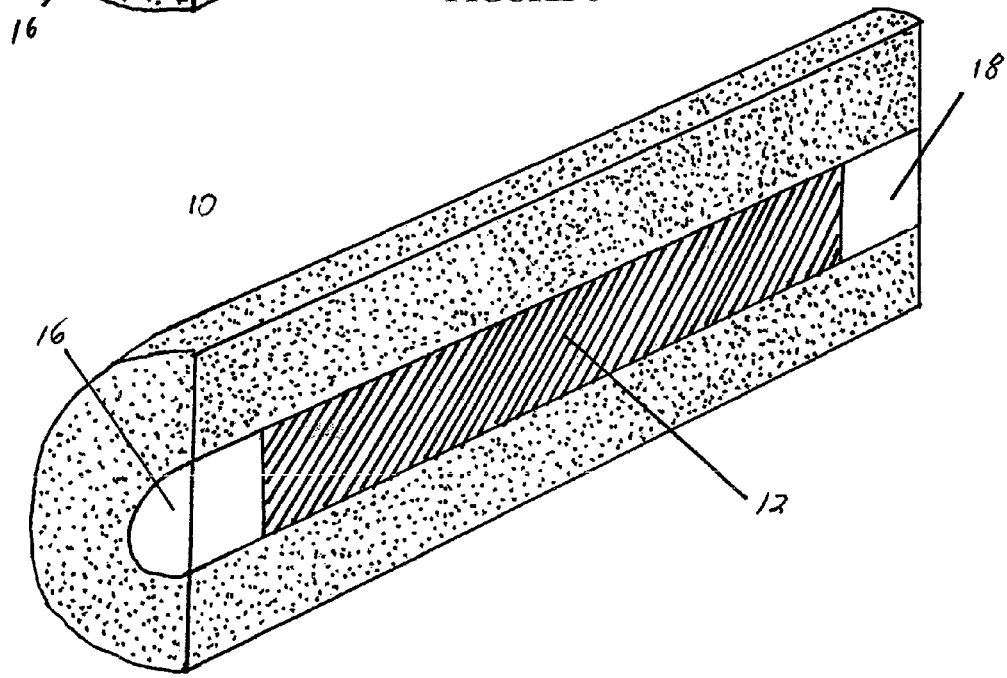
FIG. 6 is a schematic cross-sectional view taken longitudinally of a radiopaque implant having an inner core whose ends are capped.

In another embodiment, depicted in FIG. 6, the ends of the inner core 16, 18 are capped. This occurs when the radiopaque material is added to the silicone intermittently rather than continuously. The inner core 12 is divided up into solid segments wherein segments of radiopaque material alternate with segments of solid silicone such that one or more of the implant ends 16, 18 include either silicone or the radiopaque material.

One consideration when choosing a radiopaque material for use in the present invention is magnetic resonance imaging (MRI) compatibility. If the radiopaque material selected is not MRI-compatible, the implant may be contraindicated in certain situations because the magnetic field present in the MRI environment may result in movement or heating of the implant. Tantalum is a preferred radiopaque material in the present invention because it is not ferromagnetic, i.e., it will not experience significant translational force or torque when exposed to strong magnetic fields, such as MRI. Furthermore, because the magnetic susceptibility of tantalum is very low, tantalum used in the quantities needed to fabricate the implant will not produce significant image artifacts. Tantalum is also often used in many types of medical devices, such as orthopedic and dental implants and is well-understood in the field of material science. For these reasons, tantalum is a preferred radiopaque material according to the present invention.

One design consideration in making embodiments of the present invention is that the use of more radiopaque material will result in greater radiopacity. The amount of radiopaque material that may be used to form the implant is only limited by the amount of silicone or other materials needed to process the radiopaque material into an implant. It is preferred to add tantalum to the silicone in the inner core 12 of the implant 10 by blending about 15% tantalum by volume to the matrix material. However, blending anywhere from 0% to 20% tantalum by volume of matrix material will result in a manufacturable radiopaque implant.

The radiopaque material may also be a filament that is added to the inner core 12 of the implant 10. Examples of radiopaque materials suitable for use as a filament in this invention include: platinum, iridium, tungsten, tantalum, silver, stainless steel, rhenium, barium, gold, and other metals that are well-known to those skilled in the art to be radiopaque. Alloys of any of the above-mentioned metals, such as platinum-iridium alloy, may also be suitable for use in this invention. These materials may be used to form filaments using techniques known in the art, which may be added to the silicone during processing of the implant.

Figure 4:
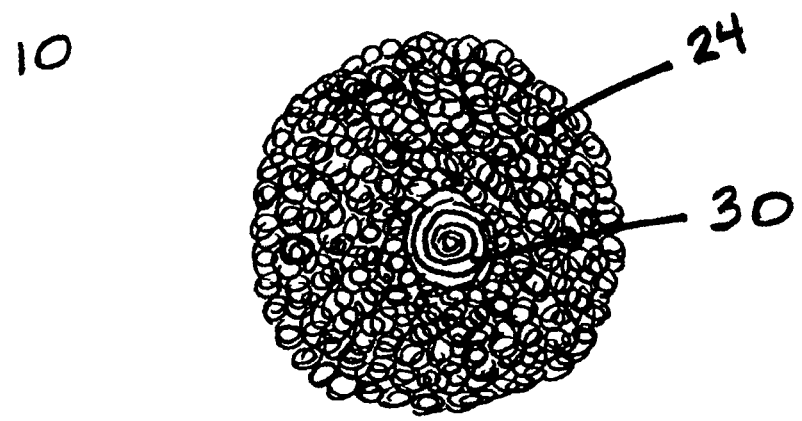
FIG. 4 is a schematic cross-sectional view taken radially of a radiopaque implant having an inner core with coiled metallic filaments.

One embodiment of the present invention is shown in FIG. 4, in which the implant 10 has one or more filaments 30 in the inner core 12 of the implant 10 having a silicone foam outer porous portion 24. In this embodiment, the filaments 30 are coiled. Each filament 30 is confined to the inner core 12 of the implant 10 and does not extend into the silicone foam outer porous portion 24. Preferably, the filaments 30 have a diameter from about 0.1 mm to 0.5 mm.

The filaments used in this invention may be a variety of different shapes and sizes. For example, the filaments may be either straight or coiled. Coiled filaments may have either a varied pitch or a consistent pitch throughout the inner core of the implant. Filaments may have a consistent length or an inconsistent length throughout the inner core of the implant. Filaments may have a consistent diameter or an inconsistent diameter throughout the inner core of the implant. The filaments described herein for use in the present invention may be obtained from a variety different sources all of which will be known to a person of ordinary skill in the art.

According to the present invention, a female patient may be sterilized by ablating the tissue within the fallopian tube using techniques known in the art, placing the radiopaque implant adjacent to the ablated tissue and then visualizing the radiopaque implant to confirm the presence of the implant within the fallopian tube. See, e.g., U.S. Pat. Nos. 6,309,384 and 6,780,182, and U.S. patent application Ser. No. 12/692,057, all of which are incorporated herein by reference in their entireties for all purposes. This method of sterilizing a female patient further comprises permitting tissue growth around the implant within the fallopian tube and subjecting the fallopian tube to fluoroscopic imaging at about six weeks and up to about twenty-six weeks post-implantation to confirm occlusion of the fallopian tube.

An HSG may be performed after the implantation to confirm placement of the implant in the fallopian tube and occlusion of the fallopian tube. The HSG provides the patient assurance that the implant is working as a method of sterilization. The HSG is usually scheduled three months after the implant procedure. If the location of the implant in the fallopian tube is satisfactory and the fluoroscopic image provides evidence that both fallopian tubes are occluded then the patient may rely on the implant and will be considered sterilized. To sterilize a female patient, the implant procedure must be performed in both fallopian tubes.

HyCoSy may be performed after the implantation to confirm placement of the implant in the fallopian tube and occlusion of the fallopian tube. The HyCoSy provides the patient assurance that the implant is working as a method of sterilization. HyCoSy, or another ultrasound procedure, employs at least one gas pocket that will reflect sound, i.e., is detectable via ultrasound.

Figure 7:
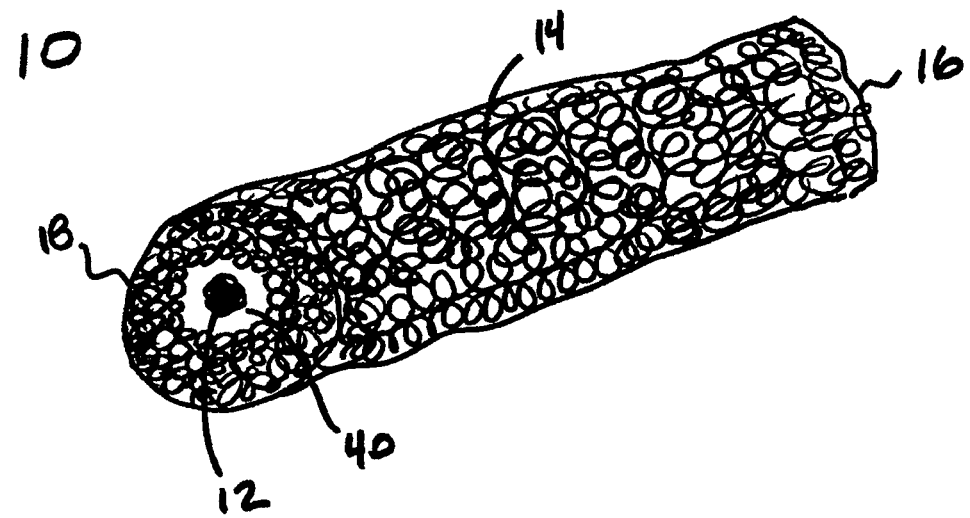
FIG. 7 is a highly-enlarged schematic perspective view of an implant according to one embodiment of the invention employing an ultrasound-detectable gas pocket along the length of the implant.
Figure 8:
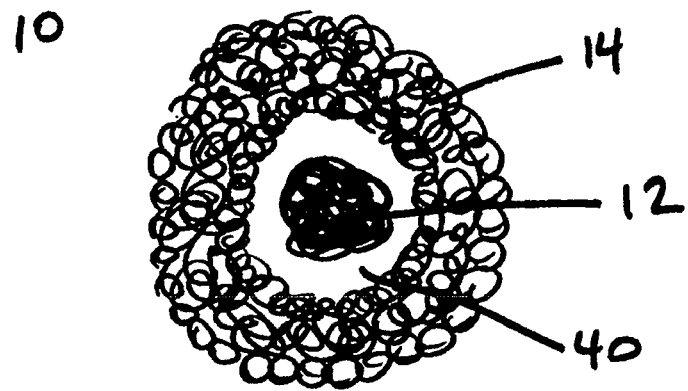
FIG. 8 is a schematic cross-section view taken radially of an implant according to one embodiment of the invention employing an ultrasound-detectable gas pocket along the length of the implant.

In some embodiments, the core of implants of the present invention are filled with slugs of silicone, as depicted in FIGS. 7 and 8, and render them detectable via ultrasound. For example, a first injection of liquid silicone can create the outer porous portion of the implant and a hollow implant core. A second injection of liquid silicone is performed so as to not completely fill the core, but to leave gas gaps along the length of the implant.

Referring to an embodiment of the present invention shown in FIG. 7 and FIG. 8, the implant includes gas pocket(s) 40 along its length. The gas pocket(s) 40 are preferably located between the inner core 12 and the outer porous portion 14, as shown in FIGS. 7 and 8, and under the implant detectable via ultrasound.

Another way in which to make an implant detectable via ultrasound is to create microbubbles in the liquid silicone that is used for the implant core. For example, a first injection of silicone without bubbles is used to create the outer porous portion and a hollow implant core. A second injection of liquid silicone that contains microbubbles will then fill the hollow core. The microbubbles are established when the silicone is fabricated.

Yet another way in which to make an implant detectable via ultrasound is to mix hollow microspheres with liquid silicone and use the mixture for the core of the implant. For example, small, hollow microspheres, such as those made of glass, polystyrene, or similar materials may be used.

Figure 9:
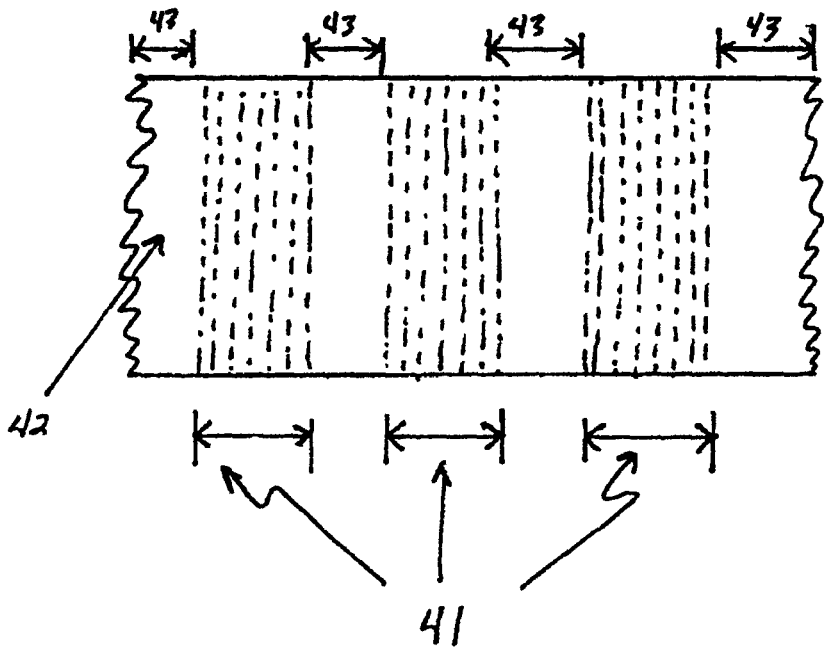
FIG. 9 is a perspective view of a highly echogenetic embodiment of the invention containing multiple echogenetic regions.
Figure 10:
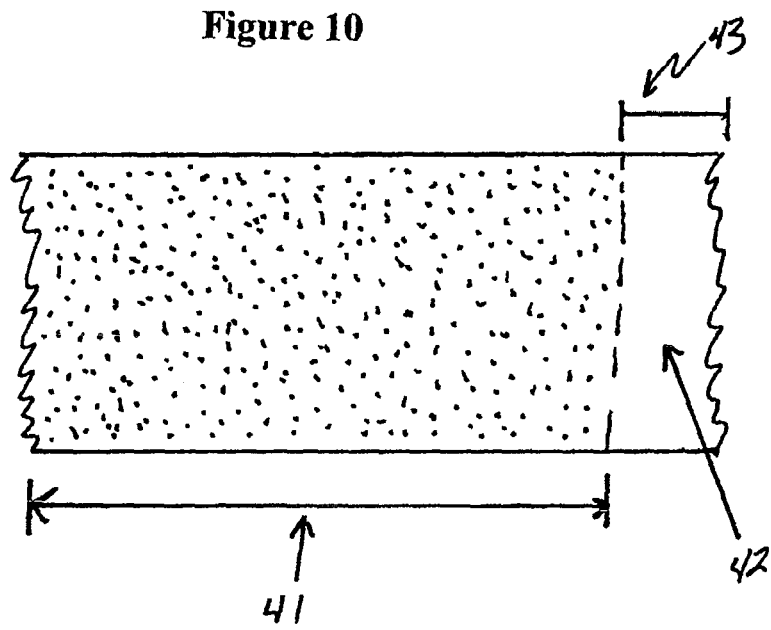
FIG. 10 is a perspective view of a highly echogenetic embodiment of the invention containing a distinct area of high echogenecity.

Referring to embodiments of the present invention shown in FIG. 9 and FIG. 10, an implant 42 can be produced to have echogenic regions and possess a defined ultrasonic signature. The regions of the implant 42 may have multiple areas of relatively high echogenicity 41 as shown in FIG. 9 or large/widened areas of high echogenicity 41 as shown in FIG. 10 that are distinct from those areas having a lower echgenicity 43. These defined areas within the implant provide an image that is distinct from background tissues and fluids (e.g. HyCoSy fluid).

Figure 11:
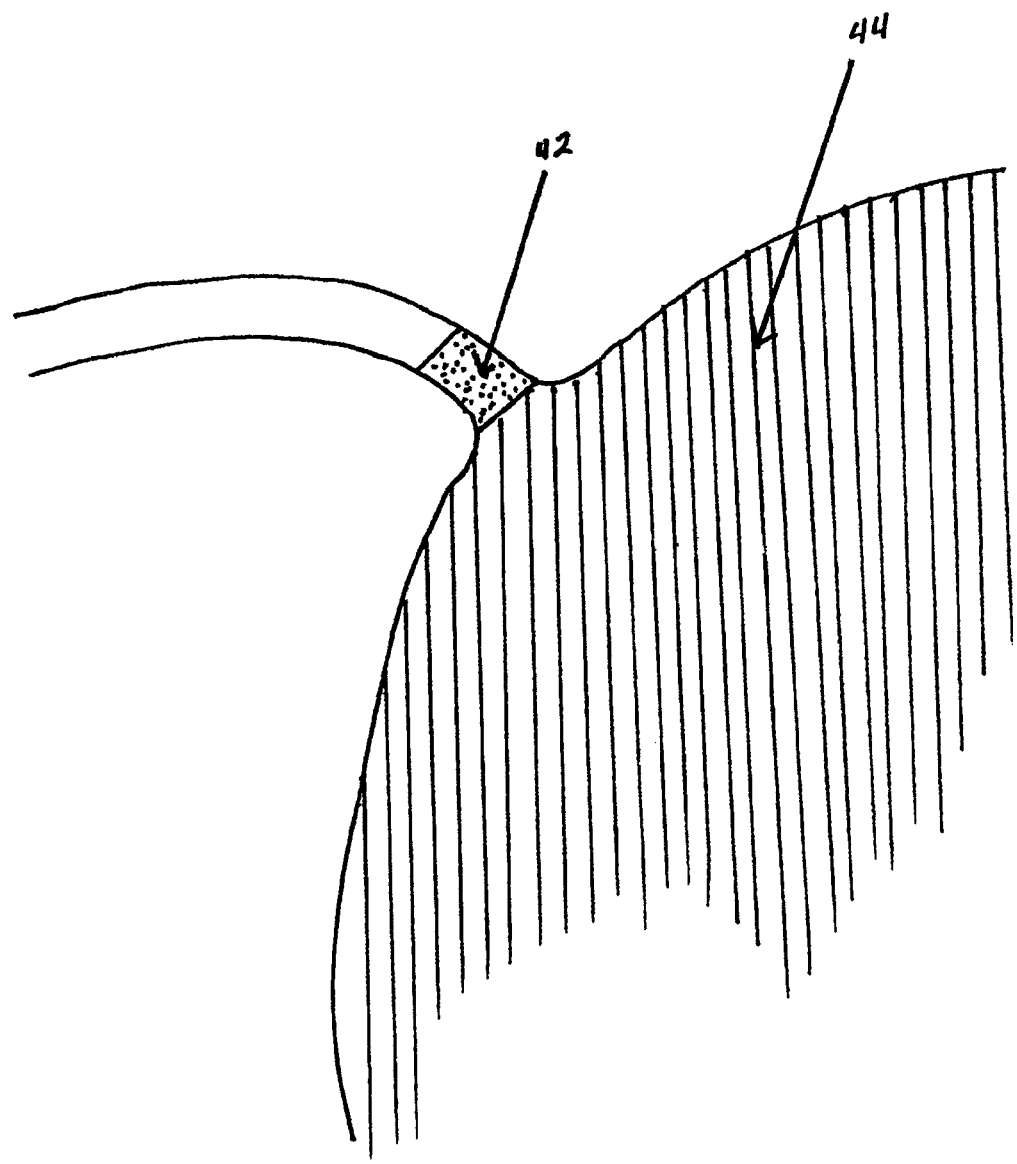
FIG. 11 is a view of an implant of the present invention after placement in a patient demonstrating the echogenecity of the implant in comparison to surrounding tissue and fluid.
Figure 12:
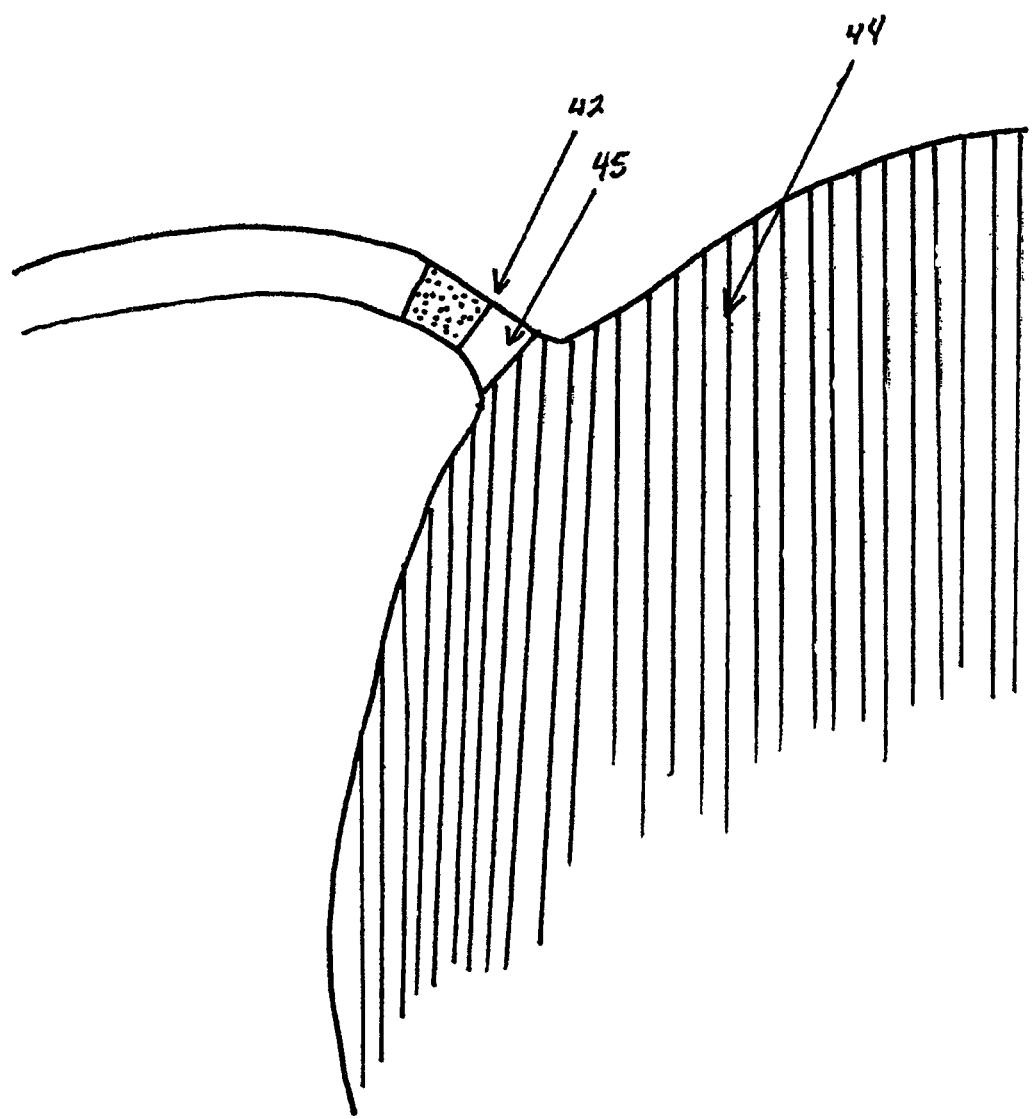
FIG. 12 is a view of an implant of the present invention having high and low echogenicity after placement in a patient demonstrating the echogenecity of the implant in comparison to surrounding tissue and fluid.

Referring to FIG. 11 and FIG. 12, the implant 42 is characterized by an echogenic signature that may be tuned to distinguish it from the surrounding tissue and HyCoSy fluid 44. As shown in FIG. 11, the image may show HyCoSy fluid 44 in contact with the implant 42 while at the same time providing an image that distinguishes the implant from the HyCoSy fluid 44. FIG. 12 demonstrates an embodiment where the echogenetic enhancement is omitted from the proximal portion 45 of the implant 42 such that the proximal portion 45 is not as detectable as the remainder of implant 42. The benefit of such an embodiment provides a means to determine whether occlusion has occurred in a HyCoSy procedure as the image would show the highly echogenic fluid in contact with the low echogenetic proximal end 45 of the implant 42 while at the same time showing the highly echogenetic distal end of the implant 42.

EXAMPLES

Sample implants made of different types of filaments were tested for visibility using fluoroscopic visualization techniques.

Example 1

Six implants were constructed each having a silicone outer porous portion and a radiopaque inner core made of coiled metal filaments. One implant had iridium coiled filaments, one implant had platinum coiled filaments, one had platinum-iridium coiled filaments, one had gold coiled filaments, one had tantalum coiled filaments, and one had rhenium coiled filaments. The coils were constructed by winding the filaments around a polyamid tube with a mandrel inside, reflowing polyurethane over it, and removing the mandrel. The coiled filaments in each implant had a length of 3 mm, a diameter of about 0.004 inches to 0.005 inches, and a pitch of about 0.004 inches to 0.005 inches.

The implants were imaged twice. For the first image, a small, office-sized fluoroscope was used. For the second image, the implants were inserted into a human cadaver and a larger, operating room-sized fluoroscope was used.

All implants were visible in both fluoroscopic images. The implant employing platinum coiled filaments exhibited the greatest detectability.

Example 2

Twelve implants were constructed each having a silicone outer porous portion and a radiopaque inner core made of coiled platinum. The filament diameter, spacing, pitch, and mandrel diameter were as follows:

| Material | Filament Diameter | Spacing | Pitch | Mandrel Diameter |
| --- | --- | --- | --- | --- |
| Platinum | 0.002" | 0" | 0.002" | 0.009" |
| Platinum | 0.005" | 0.005" | 0.010" | 0.009" |
| Platinum | 0.004" | 0" | 0.004" | 0.009" |
| Platinum | 0.005" | 0.0025" | 0.0075" | 0.009" |
| Platinum | 0.010" | 0" | 0.010" | 0.009" |
| Platinum | 0.005" | 0.010" | 0.015" | 0.009" |
| Platinum | 0.003" | 0" | 0.003" | 0.009" |
| Platinum | 0.003" | 0.006" | 0.009" | 0.009" |
| Platinum | 0.003" | 0.0015" | 0.0045" | 0.009" |
| Platinum | 0.002" | large | large | 0.009" |
| Platinum | 0.003" | 0.003" | 0.006" | 0.009" |
| Platinum | 0.005" | 0" | 0.005" | 0.009" |

The implants were imaged twice. For the first image, a small, office-sized fluoroscope was used. For the second image, the implants were inserted into a human cadaver and a larger, operating room-sized fluoroscope was used.

All implants were visible in both fluoroscopic images. In general, the implants with larger wire diameters and smaller pitches were more detectable than smaller wire diameters and larger pitches.

Example 3

Eight implants were constructed each having a silicone outer porous portion and a radiopaque inner core made of substantially straight, metal wire segments. All implants were 3 mm in length, but ranged in material and diameter as shown in the following table:

| Material | Filament Diameter |
| --- | --- |
| Rhenium | 0.004" |
| Tantalum | 0.005" |
| Gold | 0.005" |
| Iridium | 0.005" |
| Platinum | 0.010" |
| Platinum | 0.005" |
| Platinum | 0.004" |
| Platinum | 0.002" |

The implants were imaged twice. For the first image, a small, office-sized fluoroscope was used. For the second image, the implants were inserted into a human cadaver and a larger, operating room-sized fluoroscope was used.

All implants were visible in both fluoroscopic images. The implant employing the 0.010" platinum wire exhibited the greatest detectability.

Example 4

Eleven implants were constructed each having a silicone outer porous portion and a radiopaque inner core made of a blend of metal powder and silicone, as shown in the following table:

| Powder Type | Volume | Silicone Type |
|---|---|---|
| Tungsten | 5.0% | MED-4860 |
| Tungsten | 6.5% | MED-4860 |
| Barium Sulfate | 11.3% | MED-4860 |
| Tungsten | 8.4% | MED-4860 |
| Tungsten | 8.5% | MED-4840 |
| Tungsten | 10.4% | MED-4840 |
| Tungsten | 12.2% | MED-4840 |
| Tungsten | 13.9% | MED-4840 |
| Tungsten | 10.5% | MED-4850 |
| Tungsten | 5.5% | MED-4860 |
| Barium Sulfate | 30.1% | MED-4850 |

The implants were imaged twice. For the first image, a small, office-sized fluoroscope was used. For the second image, the implants were inserted into a human cadaver and a larger, operating room-sized fluoroscope was used.

All implants were visible in both fluoroscopic images. The implants employing tungsten exhibited greater detectability than implants with barium sulfate and implants employing the highest amount of tungsten exhibited the greatest detectability.

SUMMARY

Testing of the foregoing implants showed that radiopaque inner cores made of standard coils of different metals were equally detectable under fluoroscopy. In the tested implants, differences were observed among the radiopaque inner cores made of platinum wire of different diameters and different pitches. Platinum coils having larger wires or smaller coil spacing were more discernible under fluoroscopy than were platinum coils having smaller wires or greater coil spacing. While the implants employing straight wire were detectable, detection was greater for implants employing coils. Implants employing metal powder and silicone cores were equally detectable under fluoroscopy as were the implants employing metal coils.

While embodiments of the present invention have been shown and described, various modifications may be made without departing from the scope of the present invention.

What is claimed is:

1. An implant for placement within a fallopian tube of a patient, the implant comprising:
    an inner core comprising a radiopaque material, the radiopaque material comprising tantalum; and
    an outer porous portion at least partially covering said inner core,
    wherein said radiopaque material comprises metal particles in a matrix material, and the inner core comprises no more than 20% by volume of tantalum.

2. The implant of claim 1, wherein said radiopaque material comprises at least one substantially straight metallic wire.

3. The implant of claim 2, wherein said at least one substantially straight metallic wire is selected from the group consisting of platinum, iridium, gold, tantalum, and rhenium.

4. The implant of claim 1, wherein said matrix material comprises silicone.

5. The implant of claim 1, wherein said radiopaque material comprises a metallic coil.

6. The implant of claim 1, where said radiopaque material is placed in specific locations to produce regions of relatively high echogenicity.

* * * * *